US012039007B2

United States Patent
Ghose et al.

(10) Patent No.: US 12,039,007 B2
(45) Date of Patent: Jul. 16, 2024

(54) SYSTEMS AND METHODS OF AUTOMATIC MEDICAL IMAGE LABELING (71) Applicant: GE Precision Healthcare LLC, Wauwatosa, WI (US)

(72) Inventors: Soumya Ghose, Niskayuna, NY (US); Dattesh Dayanand Shanbhag, Bagalore (IN); Chitresh Bhushan, Schenectady, NY (US); Andre De Almeida Maximo, Rio de Janeiro (BR); Radhika Madhavan, Niskayuna, NY (US); Desmond Teck Beng Yeo, Clifton Park, NY (US); Thomas Kwok-Fah Foo, Clifton Park, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 534 days.

(21) Appl. No.: 17/067,179

(22) Filed: Oct. 9, 2020

(65) Prior Publication Data
US 2022/0114389 A1   Apr. 14, 2022

(51) Int. Cl.
*G06F 18/214* (2023.01)
*G06F 18/211* (2023.01)
(Continued)

(52) U.S. Cl.
CPC ........ *G06F 18/2148* (2023.01); *G06F 18/211* (2023.01); *G06F 18/2155* (2023.01);
(Continued)

(58) Field of Classification Search
CPC ............... G06F 18/2148; G06F 18/211; G06F 18/2155; G06F 18/22; G06F 18/232; G16H 30/40; G06V 2201/03; G06N 3/08
See application file for complete search history.

(56) References Cited

U.S. PATENT DOCUMENTS 9,183,173 B2 * 11/2015 Yih .................. G06N 20/00
2007/0116357 A1 * 5/2007 Dewaele .............. G06T 7/12
382/128
(Continued)

FOREIGN PATENT DOCUMENTS

WO    WO-2017040691 A1 *  3/2017  ......... G06K 9/00637

OTHER PUBLICATIONS

Peroni M et al. WE-E-213CD-02: "Gaussian Weighted Multi-Atlas Based Segmentation for Head and Neck Radiotherapy Planning." Med Phys. Jun. 2012;39(6Part27):3959. doi: 10.1118/1.4736158. PMID: 28519983.
(Continued)

*Primary Examiner* — Qun Shen
(74) *Attorney, Agent, or Firm* — Armstrong Teasdale LLP (57) ABSTRACT

A computer-implemented method of automatically labeling medical images is provided. The method includes clustering training images and training labels into clusters, each cluster including a representative template having a representative image and a representative label. The method also includes training a neural network model with a training dataset that includes the training images and the training labels, and target outputs of the neural network model are labels of the medical images. The method further includes generating a suboptimal label corresponding to an unlabeled test image using the trained neural network model, and generating an optimal label corresponding to the unlabeled test image using the suboptimal label and representative templates. In addition, the method includes updating the training dataset using the test image and the optimal label, retraining the neural network model, generating a label of an unlabeled image using the retrained neural network model, and outputting the generated label.

18 Claims, 9 Drawing Sheets
(5 of 9 Drawing Sheet(s) Filed in Color)

(51) Int. Cl.
*G06F 18/22* (2023.01)
*G06F 18/232* (2023.01)
*G06N 3/08* (2023.01)
*G16H 30/40* (2018.01)

(52) U.S. Cl.
CPC ............ *G06F 18/22* (2023.01); *G06F 18/232* (2023.01); *G06N 3/08* (2013.01); *G16H 30/40* (2018.01); *G06V 2201/03* (2022.01)

(56) References Cited

U.S. PATENT DOCUMENTS

| | | | | |
|---|---|---|---|---|
| 2010/0329556 | A1* | 12/2010 | Mitarai | G06V 10/7715 |
| | | | | 382/224 |
| 2017/0076438 | A1* | 3/2017 | Kottenstette | G06V 20/176 |
| 2017/0109882 | A1* | 4/2017 | Case | A61B 6/03 |
| 2017/0124727 | A1* | 5/2017 | Amat Roldan | G01B 11/14 |
| 2017/0178349 | A1* | 6/2017 | Ketcha | G06T 7/33 |
| 2018/0276813 | A1* | 9/2018 | Gur | G06T 7/0012 |
| 2019/0371474 | A1* | 12/2019 | Borsic | A61B 34/10 |
| 2020/0175681 | A1* | 6/2020 | Ezhov | G06T 11/20 |
| 2020/0245873 | A1* | 8/2020 | Frank | A61B 5/0823 |
| 2020/0258223 | A1* | 8/2020 | Yip | G06T 11/00 |
| 2020/0321120 | A1* | 10/2020 | Neumann | G16B 50/30 |
| 2020/0380675 | A1* | 12/2020 | Golden | G06T 7/143 |
| 2021/0150671 | A1* | 5/2021 | Guo | G16H 30/20 |

OTHER PUBLICATIONS

Sharma MK et al. "Mammogram segmentation using multi-atlas deformable registration." Comput Biol Med. Jul. 2019; 110:244-253. doi: 10.1016/j.compbiomed.2019.06.001. Epub Jun. 11, 2019. PMID: 31233970.

Van der Heyden B et al. "Dual-energy CT for automatic organs-at-risk segmentation in brain-tumor patients using a multi-atlas and deep-learning approach." Sci Rep. Mar. 11, 2019;9(1):4126. doi: 10.1038/s41598-019-40584-9. PMID: 30858409; PMCID: PMC6411877.

Kim SJW et al. "Multi-atlas cardiac PET segmentation." Phys Med. Feb. 2019;58:32-39. doi: 10.1016/j.ejmp.2019.01.003. Epub Jan. 18, 2019. PMID: 30824147.

Koch LM et al. "Multi-Atlas Segmentation Using Partially Annotated Data: Methods and Annotation Strategies." IEEE Trans Pattern Anal Mach Intell. Jul. 2018;40(7):1683-1696. doi: 10.1109/TPAMI.2017.2711020. Epub Aug. 22, 2017. PMID: 28841548.

Sun L et al. "Multi-Atlas Based Methods in Brain MR Image Segmentation." Chin Med Sci J. Jun. 30, 2019;34(2):110-119. doi: 10.24920/003576.PMID: 31315752.

Li X et al. "Multi-atlas tool for automated segmentation of brain gray matter nuclei and quantification of their magnetic susceptibility." Neuroimage. May 1, 2019;191:337-349. doi: 10.1016/j.neuroimage.2019.02.016. Epub Feb. 7, 2019. PMID: 30738207; PMCID: PMC6464637.

Yang H et al. "Neural multi-atlas label fusion: Application to cardiac MR images." Med Image Anal. Oct. 2018;49:60-75. doi: 10.1016/j.media.2018.07.009. Epub Jul. 31, 20181. PMID: 30099151.

* cited by examiner

Unlabeled brain image

FIG. 3E (red) Coarse head-region

FIG. 3F (red) Coarse head-region
(yellow) Coarse brain region

FIG. 3G (green) Coarse brain region

FIG. 3H

Detailed brain sub-parts labeling
via anatomy-guided registration

FIG. 3I

More detailed brain sub-parts
labeling (very fine; sub-mm level)
via anatomy-guided registration

SYSTEMS AND METHODS OF AUTOMATIC MEDICAL IMAGE LABELING

BACKGROUND

The field of the disclosure relates generally to systems and methods of image segmentation, and more particularly, to systems and methods of automatically labeling or segmenting medical images.

Deep neural networks combine features representation and classifiers, and have been successful in solving problems in image processing, such as image segmentation. Deep neural networks, however, require a large and diverse training dataset that has been manually annotated with ground truth. This process is time consuming and expensive, and suffers variability if multiple raters of ground truth are involved. Further, a large training dataset of images creates a heavy computation load. As such, implementing, training, and inferencing through the deep neural networks may take a long period of time, such as days.

BRIEF DESCRIPTION

In one aspect, a computer-implemented method of automatically labeling medical images is provided. The method includes clustering training images and training labels of the training images into a plurality of clusters, wherein the training labels annotate anatomical structures of interest in the training images, each cluster including a representative template having a representative image of the cluster and a representative label of the representative image. The method also includes training a neural network model with a training dataset, wherein the training dataset includes the training images and the training labels, and target outputs of the neural network model are labels of the medical images. The method further includes generating a suboptimal label corresponding to an unlabeled test image using the trained neural network model, and generating an optimal label corresponding to the unlabeled test image using the suboptimal label and representative templates of the clusters. In addition, the method includes updating the training dataset using the test image and the optimal label, retraining the neural network model with the updated training dataset, generating a label of an unlabeled image using the retrained neural network model, and outputting the generated label of the unlabeled image.

In another aspect, a computer-implemented method of automatically labeling medical images is provided. The method includes clustering training images and training labels into a plurality of clusters, wherein the training labels annotate anatomical structures of interest in the training images, each cluster including a representative template having a representative image of the cluster and a representative label of the representative image. The method also includes training a neural network model with a training dataset, wherein the training dataset includes the training images and training labels, and target outputs of the neural network model are labels of the medical images. The method further includes generating a suboptimal label corresponding to an unlabeled test image using the trained neural network model, and generating an optimal label corresponding to the unlabeled test image using the suboptimal label and representative templates of the clusters.

In yet another aspect, a computer-implemented method of automatically labeling an image is provided. The method includes clustering training images and training labels into a plurality of clusters, wherein the training labels annotate structures of interest in the training images, each cluster including a representative template having a representative image of the cluster and a representative label of the representative image. The method also includes generating a suboptimal label corresponding to an unlabeled image using a segmentation model, generating an optimal label corresponding to the unlabeled image using the suboptimal label and representative templates of the clusters, and outputting the generated optimal label of the unlabeled image.

DESCRIPTION OF THE DRAWINGS

The patent or application file includes at least one drawing executed in color. Copies of this patent or patent application publication with color drawing(s) will be provided by the Office upon request and payment of the necessary fee.

DETAILED DESCRIPTION

The disclosure includes systems and methods of automatically labeling images. As used herein, a label is a mask that is used to segment out structures of interest in an image. For the purpose of detailed description, magnetic resonance (MR) images are used herein as examples only. The systems and methods described herein, however, are not limited to use in MR systems and applied to MR images, and may be applied to medical images acquired with other imaging modalities, such as computed tomography (CT). The images may be images acquired from the different modalities. The systems and methods described herein may be applied to images in general.

The systems and methods described herein automatically generate a large number of ground truth of unlabeled images without manually label all of them. A small subset of the unlabeled images is first manually labeled. The manually-labeled images and their labels are grouped into clusters represented with representative templates. Suboptimal labels of the rest of the unlabeled images are labeled with a segmentation model such as a neural network model. A neural network model is used herein as an example only. Any segmentation model that is suited for image segmentation and provides labels of the images, such as active contour models, shape prior models, or atlases may be used to generate suboptimal labels. The suboptimal labels are optimized using the representative templates. The methods described herein may be referred to as anatomy-guided registration. The automatically-generated ground truth may be used to generate labels of images of an increased accuracy, optimize machine learning models, and ensure quality of classification and segmentation systems.

Neural network models have been used to segment images. The accuracy of a neural network model largely depends on the amount data included in training datasets. The more data is provided, the higher the accuracy of inferencing by the neural network model becomes. For example, for brain image segmentation, 300 to 400 brain images would be needed in the training dataset for the neural network model to have a satisfactory accuracy in inferencing or predicting a label. In supervised learning, ground truth is provided in the training datasets. For imaging segmentation, such as medical imaging segmentation, to generate ground truth, labels or masks of anatomical structures are marked by radiologists or technologists, which is time consuming and costly.

The systems and methods disclosed herein use a multi-atlas clustering framework in combination with a neural network model to generate ground truth for training datasets and the combination creates a much reduced need for manual labeling. This combined framework also increases the accuracy in segmentation, by further fine tuning the label generated by the neural network model using the multi-atlas clustering framework. In addition, because of the complexity and data volume, image segmentation is often computation heavy, and creates a significant processing burden on systems executing the computation. The systems and methods disclosed herein significantly reduce the computation load by registering images and their labels to representative templates in the clusters and simplifying other registrations by using existing transformation parameters. Moreover, to include additional structures in the label, the systems and methods disclosed herein allow additional structures to be included in the label without starting the entire process anew, instead by manually updating the representative templates of the clusters only and then automatically updating the rest of the training dataset. Finally, anatomy-guided registration is used in the systems and methods disclosed herein to increase the accuracy in image registration. In anatomy-guided registration, a region of interest in the image that includes the anatomical structures of interest, instead of the entire image, is registered.

Figure 1A:
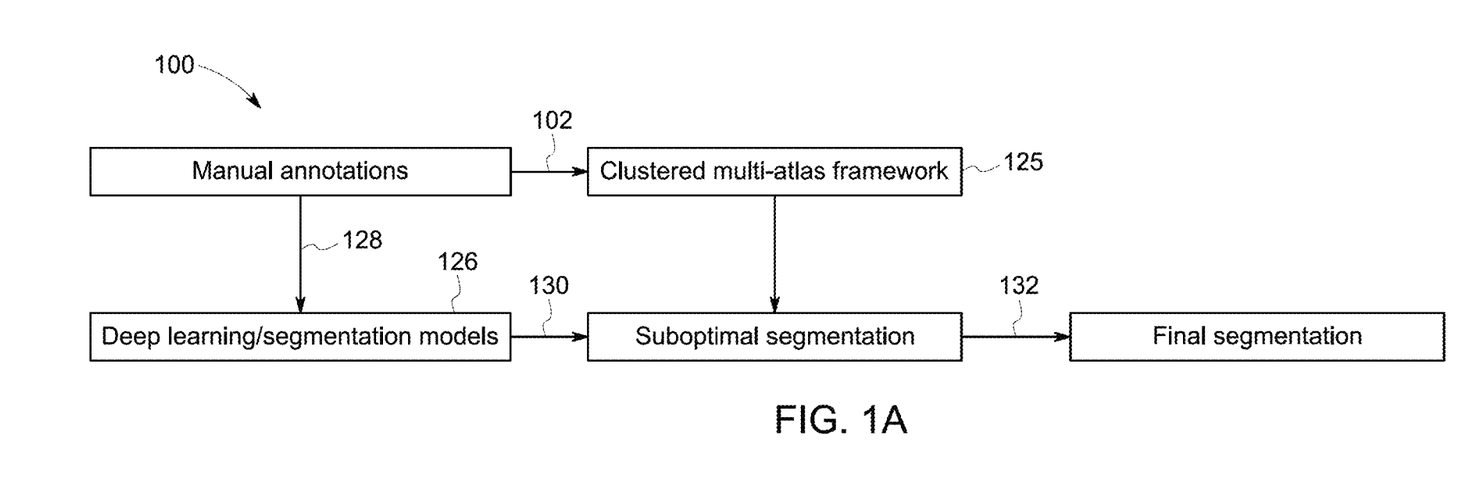
FIG. 1A is a high-level schematic diagram of an exemplary method.
Figure 1B:
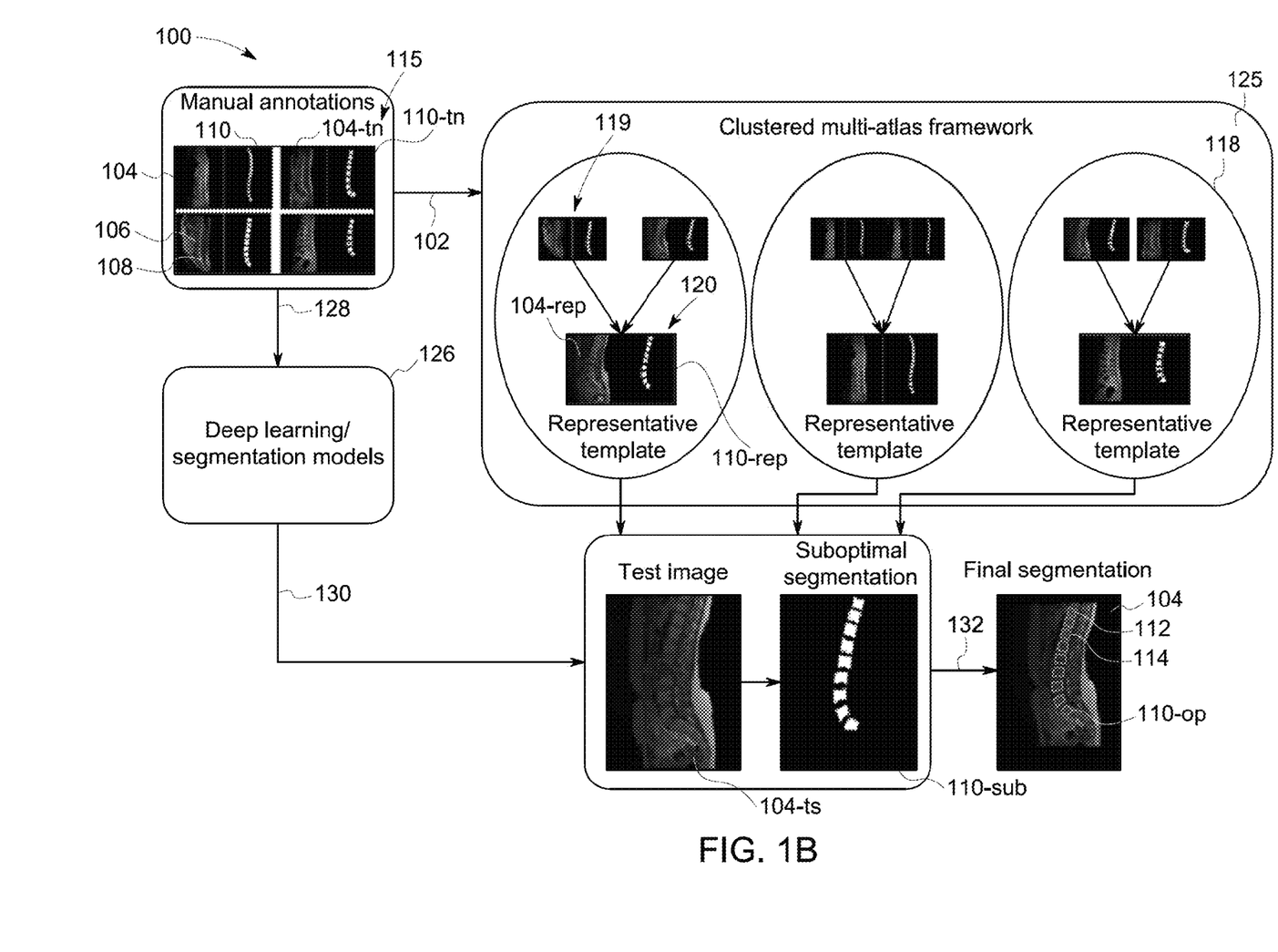
FIG. 1B is a detailed schematic diagram of the method shown in FIG. 1A.
Figure 1C:
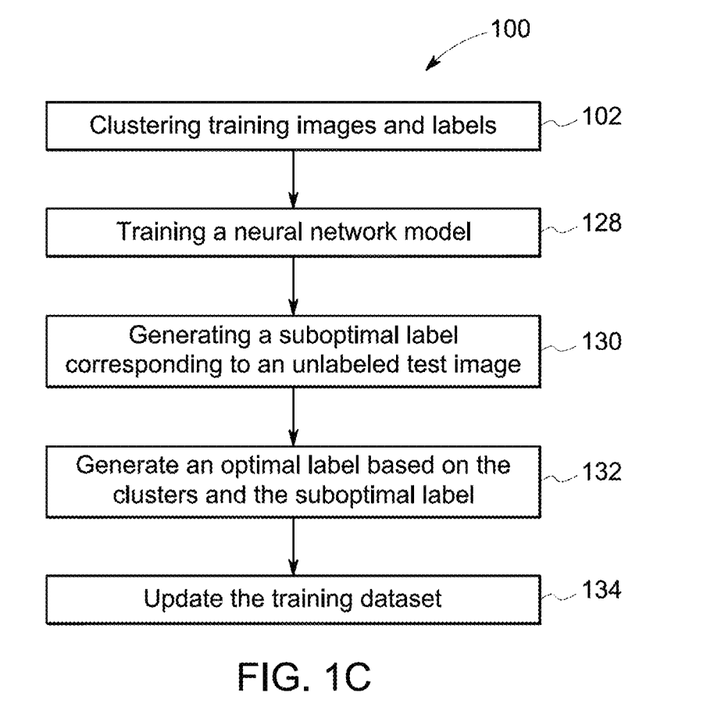
FIG. 1C is a flow chart of the method shown in FIG. 1A.
Figure 1D:
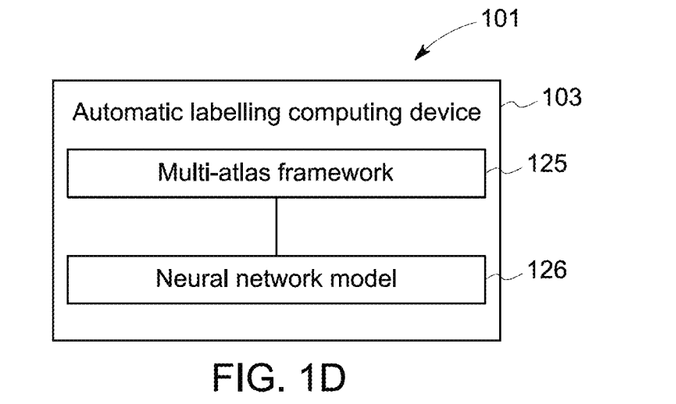
FIG. 1D is an exemplary system for implementing the method shown in FIG. 1A.

FIGS. 1A and 1B are high-level (FIG. 1A) and detailed (FIG. 1B) schematic diagrams of an exemplary method 100 of automatically labeling medical images. FIG. 1C is a flow chart of the method 100. FIG. 1D is a schematic diagram of an exemplary automatic labeling system 101 used to implement the method 100.

The method 100 includes clustering 102 training images and labels of the training images. A label is a mask for an image that indicates areas of the image having structures of interest. For example, if a medical image 104 is a MR spine image, and anatomical structures of interest are vertebrae 106, a label 110 is a mask indicating the areas in the medical image 104 that vertebrae 106 occupy. The label 110 may be used as a mask to generate an image showing a region of interest (ROI) 114 or an ROI image 112. An ROI is the region in a medical image that is of interest or includes anatomical structures of interest. In other words, a label 110 shows an ROI 114 in a medical image 104.

In the exemplary embodiment, a training dataset 115 is started with a relatively small number of training images 104-$tn$, e.g., 75 images, which are manually labeled by a rater such as a radiologist or technologist to generate training labels 110-$tn$ for the training images 104-$tn$. During clustering 102, a similarity metric is measured for each of the training images against another training image in the training dataset. A similarity metric measures the similarity between two images 104. In some embodiments, the similarity metric, such as normalized cross correlation and mutual information, is based on a comparison of the entire images. In other embodiments, the similarity metric, such as Dice similarity coefficient and surface distance, is based on the labeled structures or the ROI images. The similarity metric may also be based on features in a deep learning or traditional machine learning framework. For example, an ROI image 112 is generated by segmenting out the ROI 114 using the label 110, and the similarity metric is measured as the similarity between any two ROI images 112 of the training images 104-$tn$.

In FIG. 1B, training images 104-$tn$ and training labels 110-$tn$ are clustered into three clusters 118. A pair of a training image 104-$tn$ and its training label 110-$tn$ may be referred to as an atlas 119. The number of clusters 118 depends on the similarity among the training images 104-$tn$ and the tightness of a cluster 118, and may be in any other numbers. The tightness may be controlled by including images and labels into a cluster only when the images and labels have a similarity metric above a predetermined threshold.

In the exemplary embodiment, a representative template 120 is determined for each cluster 118. The representative template 120 includes a representative image 104-$rep$ and a corresponding label 110-$rep$ of the representative image 104-$rep$. The representative template 120 of a cluster 118 may be an atlas 119 in the cluster 118 that is closest to the cluster centroid. In one embodiment, the representative template 120 may have the highest similarity metrics with other atlases 119 in the cluster 118. In another embodiment, the representative template 120 may be a combined atlas of two or more atlases 119 that meet a predetermined criterion, e.g., having top similarity metrics with other atlases 119 in the cluster 118. A combined atlas may be an averaged image and an averaged label of individual atlases 119, or a weighted sum of the images 104-$tn$ and the training labels 110-$tn$ of individual atlases 119.

After representative templates 120 for all clusters 118 are determined, the atlases 119 may be registered to the representative templates 120 of that cluster 118 to derive transformed atlases. Registration may include rigid transformations, where the transformations include translation and rotation. Registration may also include non-rigid transformations to correct deformation of structures, such as soft tissue, depicted in an image. In the exemplary embodiment, the registration of the atlas 119 to the representative template 120 is anatomy guided. That is, the ROI image 112 of the atlas 119 is registered to the ROI image 112 of the representative template 120. The accuracy of registration is increased by anatomy-guided registration because the ROI images include only anatomical structures of interest and the derived parameters for the registration based on ROI images more accurately reflect the transformations needed than parameters based on the entire images, which may include drastically different features that unduly affect the estimation of the parameters.

In the exemplary embodiment, a neural network model 126 is executed. The neural network model 126 may be an encoder-decoder neural network, e.g., a U-net neural network. The neural network model 126 is configured to generate a label 110 of an image 104. The neural network model 126 may take images 104 as inputs and output labels 110 of the images 104. The output of the neural network model 126 may be the label 110 overlaid over the image 104.

In the exemplary embodiments, the method 100 includes training 128 the neural network model with a training dataset. The training dataset includes training images 104-$tn$ and their training labels 110-$tn$. The training dataset may be the registered training images and their labels after the clustering 102. The images in the training dataset 115 are input into the neural network model 126 and the target outputs of the neural network model 126 are the training labels 110-$tn$ of the images 104-$tn$. The neural network model 126 is adjusted during the training.

Once the neural network model 126 is trained, the neural network model 126 is used to segment images and generate labels of images. Combined with the multi-atlas framework 125, the trained neural network model 126 is also used to generate ground truth of a new dataset without further manual labeling. As a result, the training dataset 115 starts with a relatively small number of images and labels, e.g., 75 pairs of images and labels, and ends up with a significantly larger number of images and labels, e.g., 300-400 pairs of images and labels. The accuracy of a neural network largely depends on the amount data in a training dataset. The more training data is provided, the higher the accuracy of inferencing by the neural network model becomes. Accordingly, with the increased number of images and labels in the training dataset 115, the inferencing accuracy of the neural network model 126 is significantly increased. In the meantime, the neural network model 126 is optimized, after being trained with a large amount of automatically-generated images and their labels.

In the exemplary embodiment, ground truth for a test dataset that includes unlabeled test images 104-$ts$ is generated. The method 100 includes generating 130 a suboptimal label corresponding to an unlabeled test image using the trained neural network model. The method 100 further includes generating 132 an optimal label corresponding to the unlabeled test images using the suboptimal label and the representative templates. The training dataset is then updated 134 (FIG. 1C). The process of generating 130 a suboptimal label, generating 132 an optimal label, and updating 134 may be repeated for all test images 104-$ts$ in a test dataset.

Because the neural network model 126 is trained with a relatively small number of training images and labels, the output label 110-$sub$ of a test image 104-$ts$ is suboptimal. An optimal label is generated 132 using the representative templates 120. In the exemplary embodiment, representative templates 120 are registered to the test image 104-$ts$ and its suboptimal label 110-$sub$ and registered representative templates are derived. In one example, anatomy-guided registration is performed, where ROI images of the representative templates are registered to the ROI image of the test image.

The same transformations for registering images are applied in registering labels. The ROI image of the test image is generated by multiplying the test image 104-$ts$ with the suboptimal label 110-$sub$, for example by multiplying the test image 104-$ts$ with the suboptimal label 110-$sub$. The ROI image of a representative template 120 is generated by multiplying the representative image 104-$rep$ with the representative label 110-$rep$. Similarity metrics are computed between the registered representative image and the test image 104-$ts$. The similarity metrics may be based on the images, ROI images, or other features in the deep learning or machine learning framework. The optimal label 110-$op$ is computed based on the similarity metrics. In one embodiment, the optimal label is the registered label of the representative template having the highest similarity metric with the test image. In another embodiment, the optimal label 110-$op$ is a combined label of registered labels of representative templates having top similarity metrics with the test image. The combination may be an average or a weighted sum of the individual registered labels.

In some embodiments, not only the representative templates are registered to the test images, the atlases 119 in the clusters 118 are also registered to the test images. Because the atlases 119 have been registered to the corresponding representative templates 120 of the cluster, to register the atlas 119 to the test image 104-$ts$ and its suboptimal label 110-$sub$, the same transformations for registering the corresponding representative templates 120 are applied to the atlases 119. A similarity metric is computed between the transformed atlases and the test image. An optimal label 110-$op$ of the test image 104-$ts$ is chosen as the transformed label of the atlas having the highest similarity metric or a combined label that combines transformed labels of the transformed atlases that meet a predetermined criterion, e.g., having top similarity metrics. The combination may be an average or a weighted sum of the individual transformed labels.

In the exemplary embodiment, the optimal label 110-$op$ is regarded as the ground truth for the testing image 104-$ts$. The training dataset is updated 134 by including the test image and its optimal label into the training dataset. In some embodiments, the test image 104-$ts$ and its optimal label 110-$op$ are registered to the representative template 120 of the cluster 118 with which the test image 104-$ts$ has the highest similarity metric. The transformed test image and the transformed optimal label may be included in the cluster as an atlas 119. The transformed test images and the transformed optimal label may be included in the training dataset.

In operation, the number of test images 104-$ts$ is much greater than the number of training images 104-$tn$. For example, the number of test images is 300-400, while the number of training images is 75. As a result, a large number of ground truth for a training dataset are automatically generated with manual labeling of only a much smaller number of training images.

The neural network model 126 may be retrained using the updated training dataset. Compared to the original training dataset that only includes the training images 104-$tn$ and their training labels 110-$tn$, the updated training dataset has significantly increased number of images and labels. As such, the retrained neural network model 126 has an increased accuracy in inferencing. In addition to reducing the level of required manual labeling, the computation load incurred from registration is measurably reduced in the systems and methods disclosed herein. The load on the systems handling the computation is reduced primarily because the registration is needed only for registration of representative templates of the clusters to derive transformation parameters, rather than registering each atlas in the entire training dataset. The same transformations for the representative template are applied to the atlases of that cluster.

In the exemplary embodiment, the method 100 may further include segmenting anatomical structures of interest of an unlabeled image using the retrained neural network model. The label of the unlabeled image generated by the retrained neural network model may be output to a user interface. The label may be displayed by itself, or as being overlaid over the image. The labels may also be used to classify images, for example, classifying the images into categories such as cervical images or lumbar images based on the labels.

In the exemplary embodiment, the automatic labeling system 101 includes an automatic labeling computing device 103 (FIG. 1D). The computing device 103 includes the multi-atlas framework 125 and the neural network model 126. The automatic labeling system 101 may include two automatic labeling computing devices 103, with the multi-atlas framework 125 and the neural network model 126 implemented on separate automatic labeling computing device 103, which communicate with each other through wired or wireless communication.

The systems and methods disclosed herein make a multi-atlas registration tractable, where the computation load is much reduced, both in terms of labeling the atlases and labeling a large number of test images. The speed of training and inferencing has been greatly increased, allowing the time for training and inferencing to be decreased, for example, such training and inferencing could take days in known systems and now takes a couple of hours using the systems and methods disclosed herein.

Figure 2A:
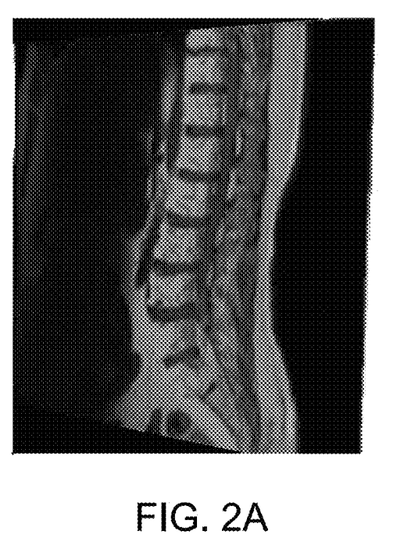
FIG. 2A is an image labeled with the method shown in FIG. 1A.
Figure 2B:
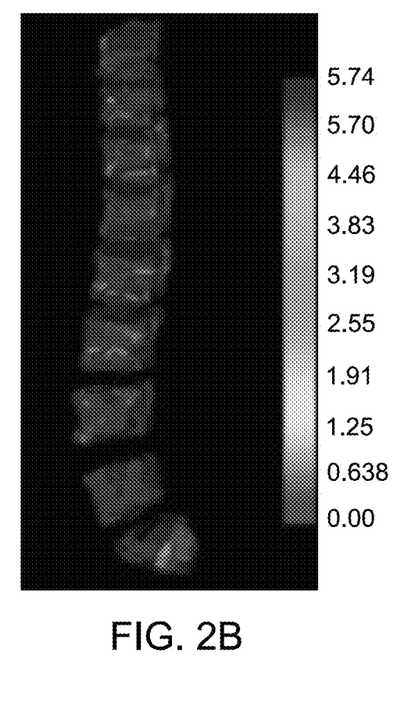
FIG. 2B illustrates errors between the label shown in FIG. 1A and a manually-generated label.

FIGS. 2A-2B show an image labeled with the method and system described herein (FIG. 2A) and the errors between the label automatically generated and manually generated (FIG. 2B). In the depicted examples, the Dice similarity coefficient (DSC) between the manually-generated label and the automatically-generated label is increased to 0.93±0.01 from 0.81±0.08 where only the multi-atlas-based framework is used. A DSC is a quotient of similarity between two samples, and its values range from 0 to 1, with 1 being assigned when the two samples are identical.

Figure 3A:
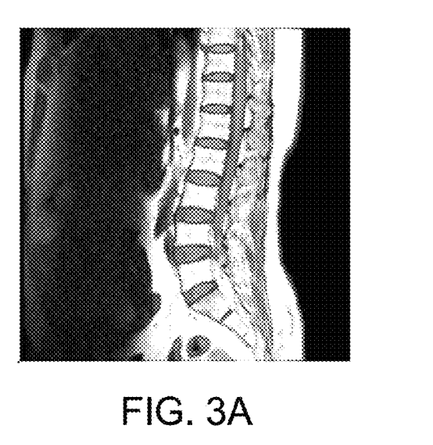
FIG. 3A is a magnetic resonance (MR) image of a spine.
Figure 3B:
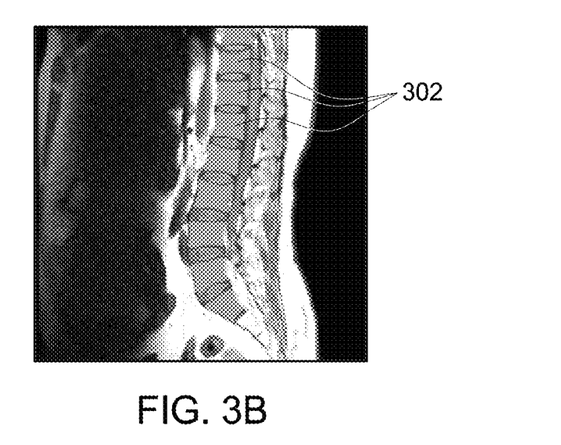
FIG. 3B is a manually-generated label of the image shown in FIG. 3A.
Figure 3C:
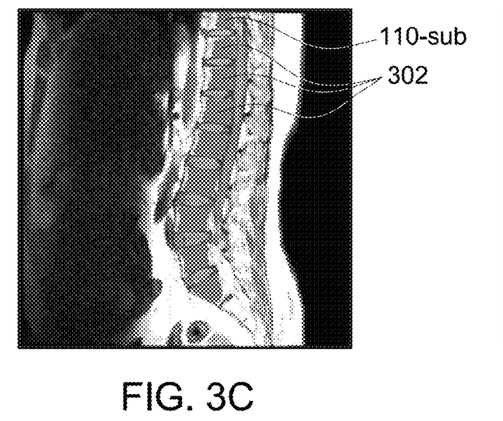
FIG. 3C is a sub-optimal label of the image shown in FIG. 3A.
Figure 3D:
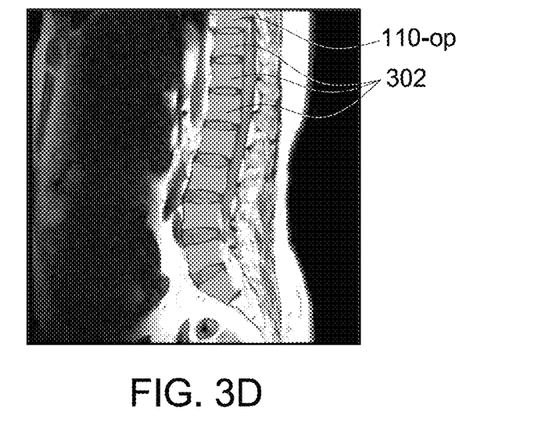
FIG. 3D is an optimal label of the image shown in FIG. 3A.

FIGS. 3A-3D show that an optimal label 110-*op* generated by the methods and system disclosed herein has a better segmentation accuracy than a suboptimal label 110-*sub*. FIG. 3A is a sagittal MR spine view. FIG. 3B shows corresponding vertebrae 302 that are manually labeled and used to compare the optimal label 110-*op* with the suboptimal label 110-*sub*. FIG. 3C shows a sub-optimal label 110-*sub* of the image shown in FIG. 3A, generated with the neural network model trained with an initial training dataset that has a small number of training images and training labels. FIG. 3D shows an optimal label 110-*op* generated with the method shown in FIG. 1A. Compared to the sub-optimal label 110-*sub*, vertebrae 302 marked by the optimal label 110-*op* closely match those manually marked in FIG. 3B, and the optimal label 110-*op* has a reduced segmentation error.

Referring back to FIGS. 1A and 1B, if additional anatomical structures of interest are needed to be labeled, using the methods and systems disclosed herein, the images in the training dataset do not need to be all relabeled. Instead, only the representative templates 120 are relabeled to include the additional anatomical structures, and the labels for the atlases 119 in the cluster 118 are derived by transforming the relabeled representative label. For example, if a spinal cord 108 needs to be included in the label 110, the representative images 104-*rep* are manually labeled to include the spinal cord 108 in the representative label 110-*rep*. The label for each atlas may be generated by transforming the relabeled representative label 1110-*rep* for the representative template to which the atlas belongs. The transformations are the inverse of the transformations applied in registering the atlas 119 to the representative template 120. Therefore, the parameters of the inverse transformations do not need to be estimated, instead being directly derived from the parameters used for registering the atlas 119 to the representative template 120. The training dataset 115 may be updated by including the images of the atlases and the relabeled labels of the atlases. The neural network model 126 may be retrained with the updated training dataset that has the additional anatomical structures labeled. As such, need of manual relabeling is largely reduced, and the computation load to update the atlases 119 and training dataset 115 is also largely reduced.

Figure 3E:
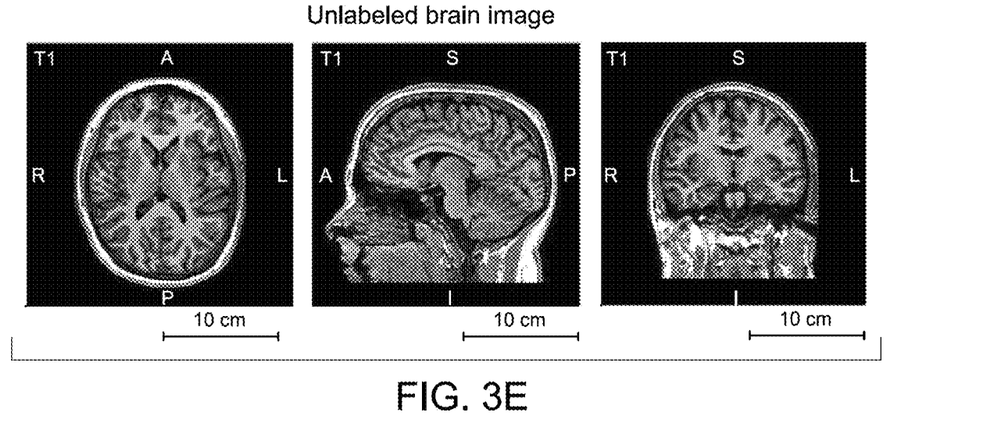
FIG. 3E shows unlabeled brain images.
Figure 3F:
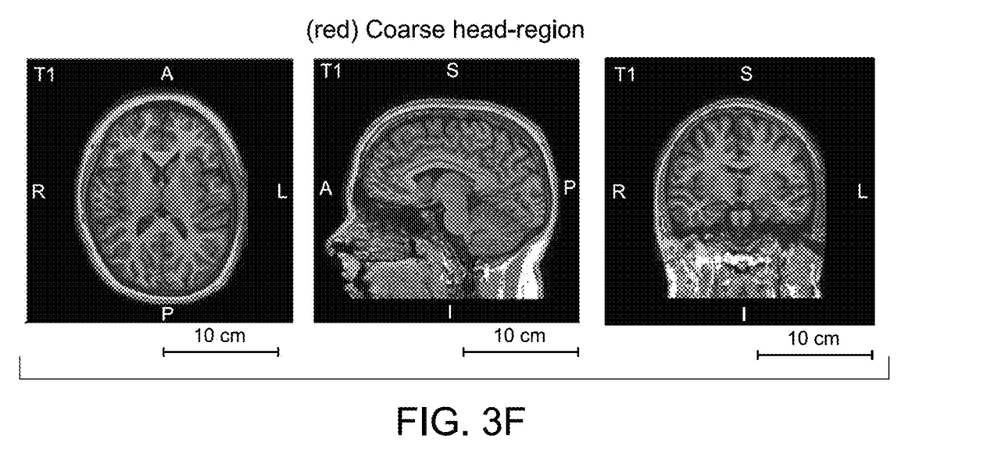
FIG. 3F shows suboptimal labels marking head regions of the images shown in FIG. 3E.
Figure 3G:
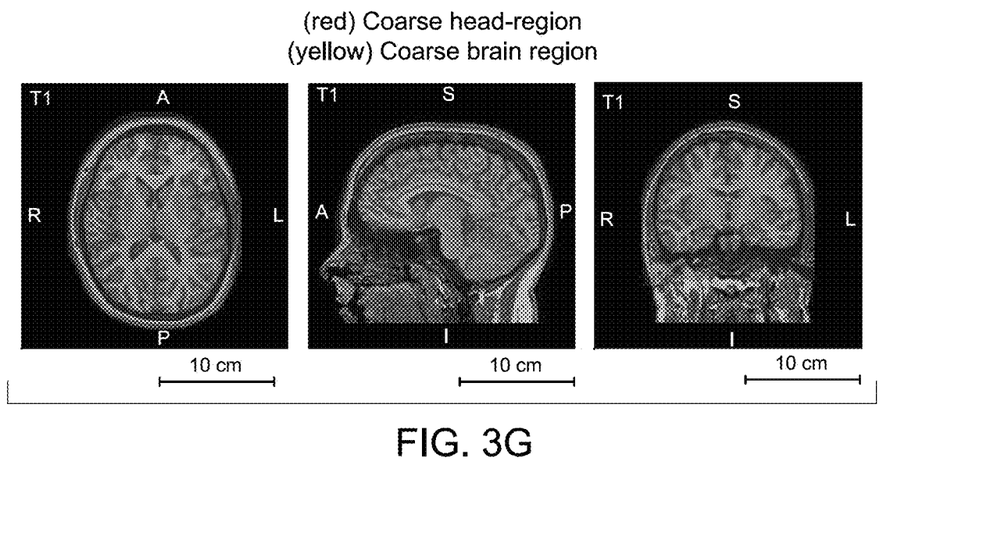
FIG. 3G shows suboptimal labels marking head and brain regions of the images shown in FIG. 3E.
Figure 3H:
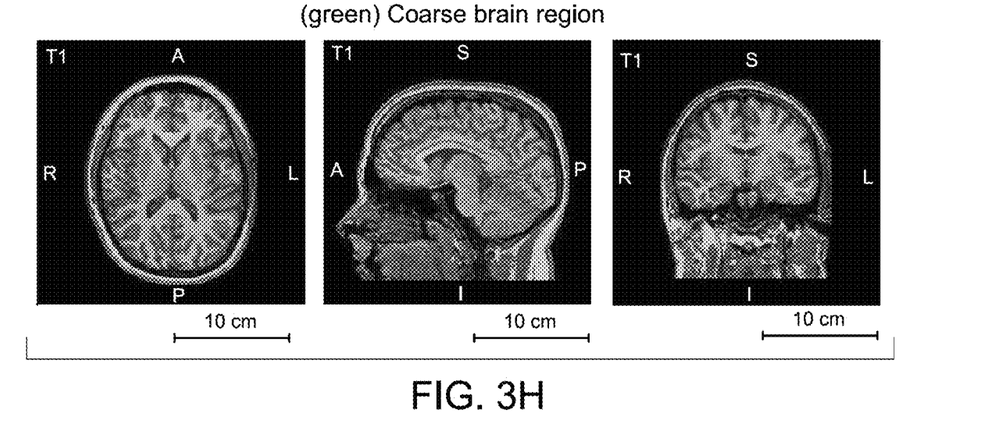
FIG. 3H shows suboptimal labels marking brain regions of the images shown in FIG. 3E.
Figure 3I:
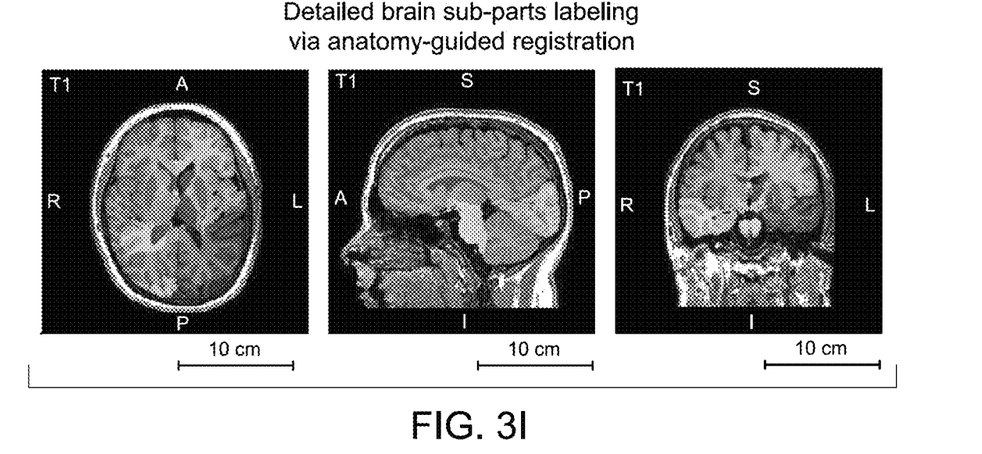
FIG. 3I shows exemplary optimal labels marking anatomical structures of the images shown in FIG. 3E.
Figure 3J:
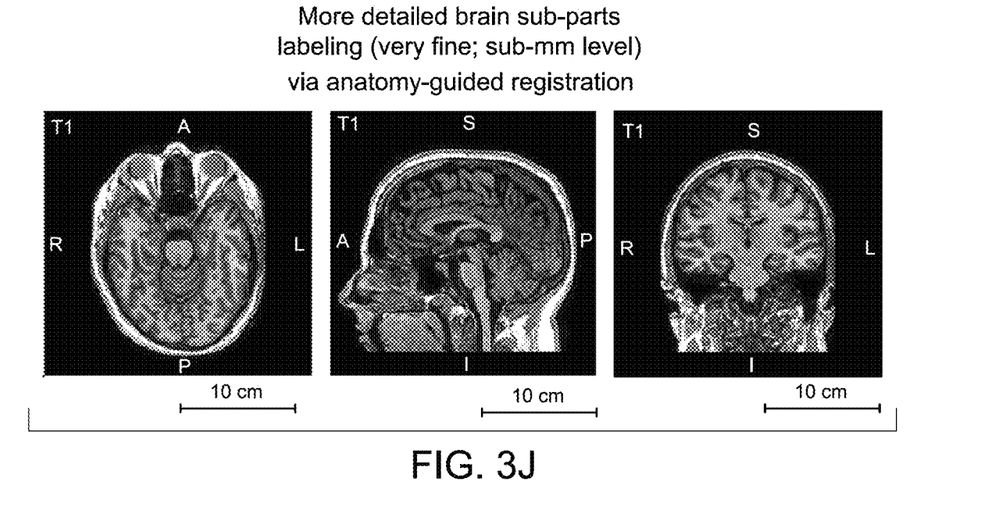
FIG. 3J shows exemplary optimal labels marking anatomical structures of the images shown in FIG. 3E, where the marked anatomical structures are finer than those marked in FIG. 3I.

MR spine images are used herein as examples only. The systems and methods described herein are not limited to spine, MR images, or medical images. The systems and methods may be used for automatically labeling other anatomical structures of interest, such as the brain, knee, shoulder, or prostate. FIGS. 3E-3J show anatomical structures in the brain are automatically labeled with the systems and methods described herein. FIG. 3E shows unlabeled brain images. FIGS. 3F-3H show those brain images overlaid with suboptimal labels of head regions and/or brain regions. FIG. 3I shows optimal labels of the brain images, showing sub-regions in the brain. FIG. 3J shows optimal labels of the brain images that mark anatomy structures at a millimeter (mm) and/or sub-mm level, such as the optical nerve and internal auditory canal, which are approximately 2-3 mm in size.

Further, the images may be medical images acquired with other image modalities, such as x-ray and CT. The images do not need to be acquired with the same modality. For example, the images may be spine images acquired with MR, x-ray, CT, and any combination thereof. The system and methods can be used to automatically label structures of interest in an image in general. In one example, the images are images of parts or defects of the machines parts manufactured and the label marks defects in the parts.

Figure 4A:
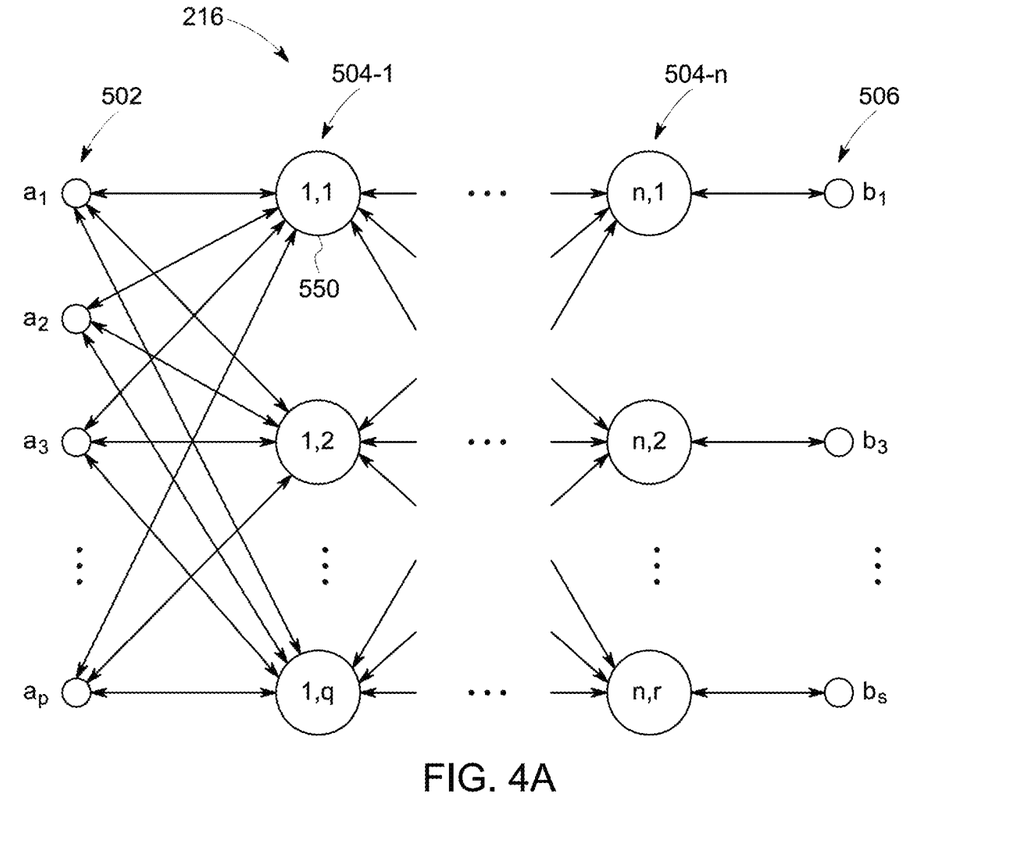
FIG. 4A is a schematic diagram of a neural network.

FIG. 4A depicts an exemplary artificial neural network model 216. The exemplary neural network model 126 includes layers of neurons 502, 504-1 to 504-*n*, and 506, including an input layer 502, one or more hidden layers 504-1 through 504-*n*, and an output layer 506. Each layer may include any number of neurons, i.e., q, r, and n in FIG. 4A may be any positive integers. It should be understood that neural networks of a different structure and configuration from that depicted in FIG. 4A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 126 changes during the training process, and some neurons are bypassed or ignored if, for example, during execution of the neural network, they are determined to be of less relevance.

In the exemplary embodiment, each neuron in hidden layer(s) 504-1 through 504-n processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 126 are obtained from a hidden layer 504-1 through 504-n in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-n may share decisions relating to labeling, with no single layer making an independent decision as to labeling.

Figure 4B:
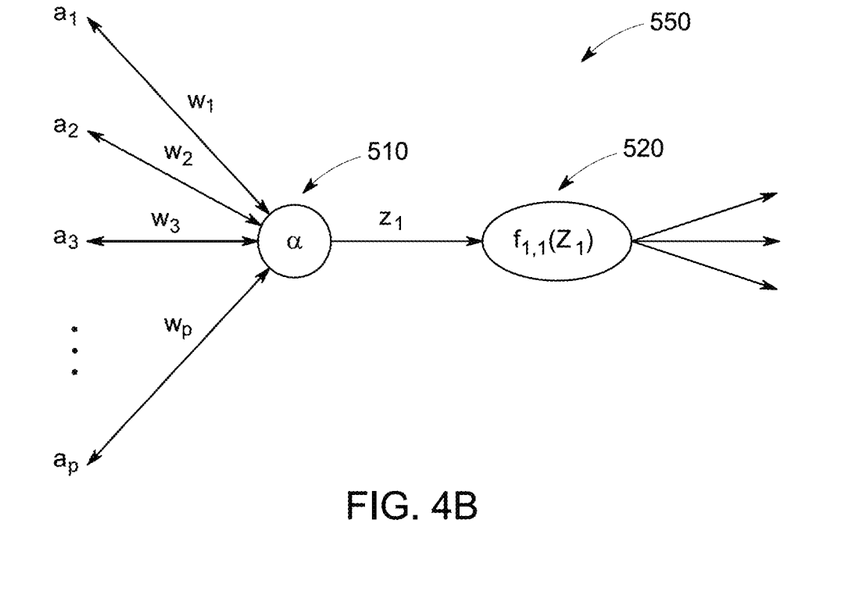
FIG. 4B is a schematic diagram of a neuron in the neural network shown in FIG. 4A.

FIG. 4B depicts an example neuron 550 that corresponds to the neuron labeled as "1,1" in hidden layer 504-1 of FIG. 4A, according to one embodiment. Each of the inputs to the neuron 550 (e.g., the inputs in the input layer 502 in FIG. 4A) is weighted such that input $a_1$ through $a_p$ corresponds to weights $w_1$ through $w_p$ as determined during the training process of the neural network model 126.

In some embodiments, some inputs lack an explicit weight, or have a weight below a threshold. The weights are applied to a function α (labeled by a reference numeral 510), which may be a summation and may produce a value $z_1$ which is input to a function 520, labeled as $f_{1,1}(z_1)$. The function 520 is any suitable linear or non-linear function. As depicted in FIG. 4B, the function 520 produces multiple outputs, which may be provided to neuron(s) of a subsequent layer, or used as an output of the neural network model 126. For example, the outputs may correspond to index values of a list of labels, or may be calculated values used as inputs to subsequent functions.

It should be appreciated that the structure and function of the neural network model 126 and the neuron 550 depicted are for illustration purposes only, and that other suitable configurations exist. For example, the output of any given neuron may depend not only on values determined by past neurons, but also on future neurons.

The neural network model 126 may include a convolutional neural network (CNN), a deep learning neural network, a reinforced or reinforcement learning module or program, or a combined learning module or program that learns in two or more fields or areas of interest. Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. The neural network model 126 may be trained using unsupervised machine learning programs. In unsupervised machine learning, the processing element may be required to find its own structure in unlabeled example inputs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics, and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Based upon these analyses, the neural network model 126 may learn how to identify characteristics and patterns that may then be applied to analyzing image data, model data, and/or other data. For example, the model 126 may learn to identify features in a series of data points.

Figure 5:
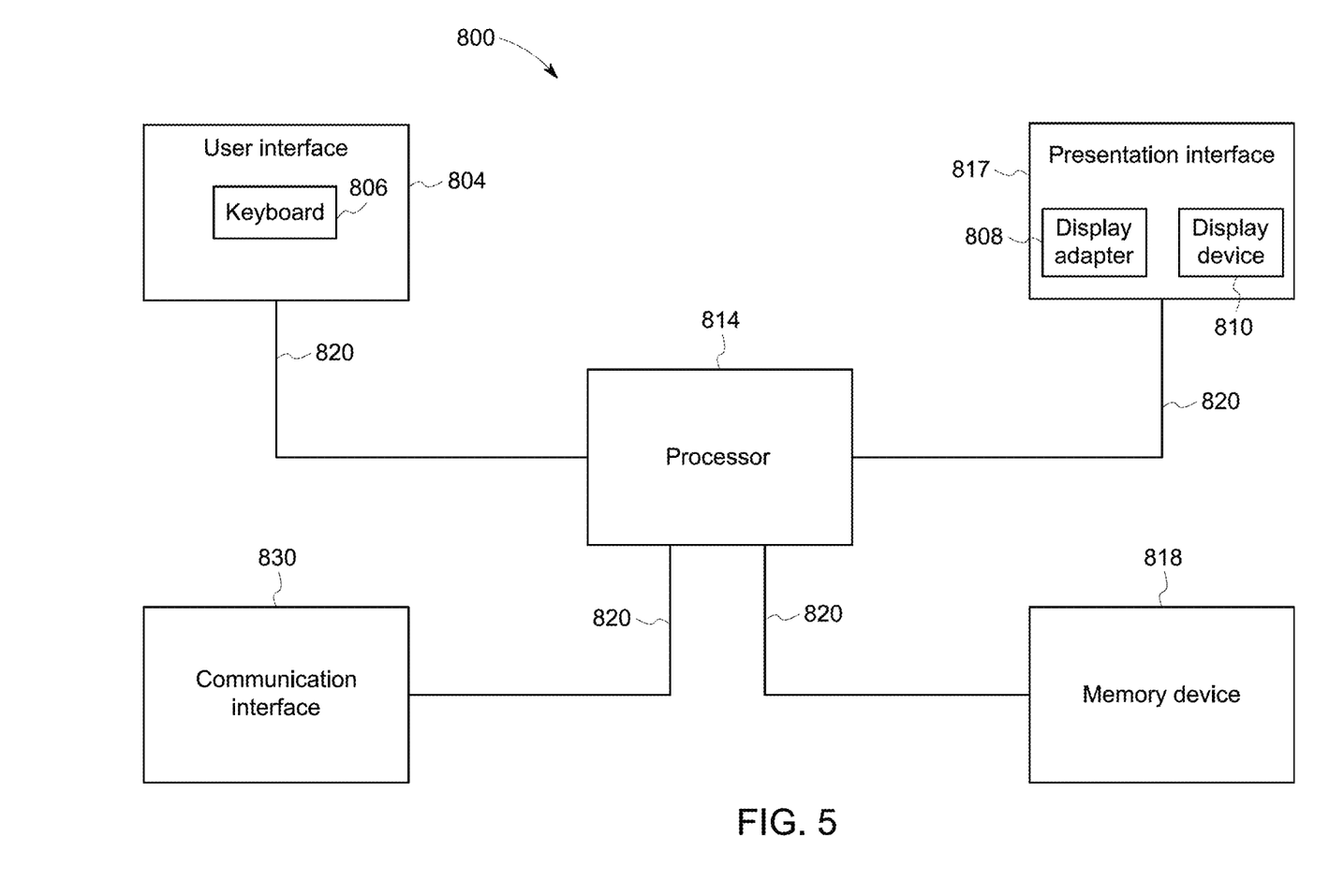
FIG. 5 is a block diagram of an exemplary computing device.

The computing device 103 described herein may be any suitable computing device 800 and software implemented therein. FIG. 5 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) automatic generation of ground truth; (b) automatic labeling of an image; (c) generation of ground truth with a much reduced need for manual labeling, (d) increased registration accuracy through anatomy-guide registration, (e) increased accuracy of labeling by combination of multi-atlas framework and a neural network model, and (0 much reduced computation load using representative templates.

Exemplary embodiments of systems and methods of automatic labeling are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of automatically labeling medical images, the method comprising:
    clustering training images and training labels of the training images into a plurality of clusters, wherein the training images include anatomical structures of interest, and wherein the training labels include masks that annotate the anatomical structures of interest in the training images, each cluster including a representative template having a representative image of the cluster and a representative label of the representative image, wherein clustering training images and training labels comprises:
    for each of the training images and training labels,
        registering each of the training images and training labels to a representative template of a corresponding cluster for each of the training images and training labels to derive transformed training images and transformed training labels; and
        registering the transformed training images and transformed training labels using parameters estimated during registering the representative image to an unlabeled test image;
    training a neural network model with a training dataset, wherein the training dataset includes the training images and the training labels, and target outputs of the neural network model are labels of the medical images;
    generating a suboptimal label corresponding to the unlabeled test image using the trained neural network model;
    generating an optimal label corresponding to the unlabeled test image using the suboptimal label and representative templates of the clusters, wherein generating the optimal label comprises:
        for each of the registered transformed training images, computing a similarity metric between each of the registered transformed training images and the unlabeled test image; and
        computing the optimal label based on the computed similarity metrics and the registered transformed training labels;
    updating the training dataset using the test image and the optimal label;
    retraining the neural network model with the updated training dataset;
    generating a label of an unlabeled image using the retrained neural network model; and
    outputting the generated label of the unlabeled image.

2. The method of claim 1, wherein clustering training images and training labels further comprises:
    for each of the training images and training labels, registering each of the training images and training labels to a representative template of a corresponding cluster for each of the training images and training labels.

3. The method of claim 2, wherein registering further comprises registering a region of interest of the training image with a region of interest of the representative image.

4. The method of claim 1, wherein generating an optimal label further comprises:
    for each of the plurality of clusters,
        registering the representative image to the unlabeled test image; and computing a similarity metric between the registered representative image and the unlabeled test image; and computing the optimal label based on the computed similarity metric.

5. The method of claim 4, wherein registering the representative image further comprises:
registering a region of interest of the representative image to a region of interest of the unlabeled test image.

6. The method of claim 4, wherein computing the optimal label comprises:
assigning the optimal label as a registered representative label of a registered representative image that has the highest similarity metric, wherein the registered representative label is generated by transforming the representative label with parameters estimated during registering the representative image to the unlabeled test image.

7. The method of claim 4, wherein computing the optimal label comprises:
assigning the optimal label as a combined label of a plurality of registered representative labels for registered representative images that have similarity metrics meeting a predetermined criterion, wherein the plurality of registered representative labels are generated by transforming the representative labels with parameters estimated during registering the representative images to the unlabeled test image.

8. The method of claim 1, wherein the anatomical structures of interest are first anatomical structures of interest, the method further comprising:
for each of the plurality of clusters,
updating the representative template by updating the representative label of the representative image, wherein the updated representative label includes the first anatomical structures of interest and second anatomical structures of interest in the representative image; and
updating training labels in the cluster by transforming the training labels using the updated representative label to derive updated labels.

9. The method of claim 8, wherein updating the training dataset further comprises replacing the training labels in the training dataset with the updated labels.

10. A computer-implemented method of automatically labeling medical images, the method comprising:
clustering training images and training labels into a plurality of clusters, wherein the training images include anatomical structures of interest, and wherein the training labels include masks that annotate the anatomical structures of interest in the training images, each cluster including a representative template having a representative image of the cluster and a representative label of the representative image, wherein clustering training images and training labels comprises:
for each of the training images and training labels,
registering each of the training images and training labels to a representative template of a corresponding cluster for each of the training images and training labels to derive transformed training images and transformed training labels; and
registering the transformed training images and transformed training labels using parameters estimated during registering the representative image to an unlabeled test image;
training a neural network model with a training dataset, wherein the training dataset includes the training images and training labels, and target outputs of the neural network model are labels of the medical images;
generating a suboptimal label corresponding to the unlabeled test image using the trained neural network model; and
generating an optimal label corresponding to the unlabeled test image using the suboptimal label and representative templates of the clusters, wherein generating the optimal label comprises:
for each of the registered transformed training images, computing a similarity metric between each of the registered transformed training images and the unlabeled test image; and
computing the optimal label based on the computed similarity metrics and the registered transformed training labels.

11. The method of claim 10, wherein clustering training images and training labels further comprises:
for each of the training images and training labels, registering each of the training images and training labels to a representative template of a corresponding cluster for each of the training images and training labels.

12. The method of claim 11, wherein registering further comprises registering a region of interest of the training image with a region of interest of the representative image.

13. The method of claim 10, wherein generating an optimal label further comprises:
for each of the plurality of clusters,
registering the representative image to the unlabeled test image; and
computing a similarity metric between the registered representative image and the unlabeled test image; and
computing the optimal label based on the computed similarity metric.

14. The method of claim 13, wherein registering the representative image further comprises:
registering a region of interest of the representative image to a region of interest of the unlabeled test image.

15. The method of claim 13, wherein computing the optimal label comprises:
assigning the optimal label as a registered representative label of a registered representative image having the highest similarity metric, wherein the registered representative label is generated by transforming the representative label with parameters estimated during registering the representative image to the unlabeled test image.

16. The method of claim 10, wherein the anatomical structures of interest are first anatomical structures of interest, the method further comprising:
for each of the plurality of clusters,
updating the representative template by updating the representative label of the representative image, wherein the updated representative label includes the first anatomical structures of interest and second anatomical structures of interest in the representative image; and
updating training labels in the cluster by transforming the training labels using the updated representative label to derive updated labels.

17. The method of claim 16, wherein updating the training dataset further comprises replacing the training labels in the training dataset with the updated labels.

18. A computer-implemented method of automatically labeling an image, the method comprising:
- clustering training images and training labels into a plurality of clusters, wherein the training images include structures of interest, and wherein the training labels include masks that annotate structures of interest in the training images, each cluster including a representative template having a representative image of the cluster and a representative label of the representative image, wherein clustering training images and training labels comprises:
- for each of the training images and training labels,
  - registering each of the training images and training labels to a representative template of a corresponding cluster for each of the training images and training labels to derive transformed training images and transformed training labels; and
  - registering the transformed training images and transformed training labels using parameters estimated during registering the representative image to an unlabeled test image;
- generating a suboptimal label corresponding to an unlabeled image using a segmentation model;
- generating an optimal label corresponding to the unlabeled image using the suboptimal label and representative templates of the clusters, wherein generating the optimal label comprises:
  - for each of the registered transformed training images, computing a similarity metric between each of the registered transformed training images and the unlabeled test image; and
  - computing the optimal label based on the computed similarity metrics and the registered transformed training labels; and
- outputting the generated optimal label of the unlabeled image.

* * * * *